US011833274B2

(12) United States Patent
Rostami et al.

(10) Patent No.: US 11,833,274 B2
(45) Date of Patent: Dec. 5, 2023

(54) OLEOPHILIC LUBRICATED CATHETERS

(71) Applicant: Hollister Incorporated, Libertyville, IL (US)

(72) Inventors: Shamsedin Rostami, South Cambridgeshire (GB); John T. Clarke, Galway (IE)

(73) Assignee: Hollister Incorporated, Libertyville, IL (US)

( * ) Notice: Subject to any disclaimer, the term of this patent is extended or adjusted under 35 U.S.C. 154(b) by 449 days.

(21) Appl. No.: 17/029,453

(22) Filed: Sep. 23, 2020

(65) Prior Publication Data

US 2021/0001011 A1    Jan. 7, 2021

Related U.S. Application Data

(63) Continuation of application No. 15/034,354, filed as application No. PCT/US2014/064254 on Nov. 6, 2014, now Pat. No. 10,821,209.

(60) Provisional application No. 61/944,173, filed on Feb. 25, 2014, provisional application No. 61/901,831, filed on Nov. 8, 2013.

(51) Int. Cl.
| | | |
|---|---|---|
| *A61L 29/08* | (2006.01) | |
| *A61L 29/04* | (2006.01) | |
| *A61L 29/06* | (2006.01) | |
| *A61M 25/00* | (2006.01) | |

(52) U.S. Cl.
CPC ............ *A61L 29/08* (2013.01); *A61L 29/041* (2013.01); *A61L 29/049* (2013.01); *A61L 29/06* (2013.01); *A61L 2300/606* (2013.01); *A61L 2400/10* (2013.01); *A61L 2420/00* (2013.01); *A61M 2025/0046* (2013.01)

(58) Field of Classification Search
CPC ....... A61M 25/0045; A61M 2025/0046; A61F 13/26; A61F 13/28; A61F 13/38; A61F 13/385; A61L 2400/10; A61L 29/08; A61L 29/085; A61L 29/141; A61L 2300/606; A61L 2300/608; A61L 2300/61; A61L 31/08; A61L 31/10
See application file for complete search history.

(56) References Cited

U.S. PATENT DOCUMENTS

| | | |
|---|---|---|
| 3,583,391 A | 6/1971 | Cox et al. |
| 3,621,848 A | 11/1971 | Magovern |
| 3,702,610 A | 11/1972 | Sheppard et al. |
| 3,861,396 A | 1/1975 | Vaillancourt et al. |
| 3,894,540 A | 7/1975 | Bonner, Jr. |
| 4,062,363 A | 12/1977 | Bonner, Jr. |
| 4,100,309 A | 7/1978 | Micklus et al. |
| 4,227,533 A | 10/1980 | Godfrey |
| 4,413,986 A | 11/1983 | Jacobs |
| 4,465,481 A | 8/1984 | Blake |
| 4,610,671 A | 9/1986 | Luther |
| 4,668,221 A | 5/1987 | Luther |
| 4,762,738 A | 8/1988 | Keyes et al. |
| 4,769,005 A | 9/1988 | Ginsburg et al. |
| 4,772,279 A | 9/1988 | Brooks et al. |
| 4,790,817 A | 12/1988 | Luther |
| 4,790,831 A | 12/1988 | Skribiski |
| 4,795,439 A | 1/1989 | Guest |
| 4,840,622 A | 6/1989 | Hardy |
| 4,883,699 A | 11/1989 | Aniuk et al. |
| 4,906,238 A | 3/1990 | Greenfeld et al. |
| 4,952,359 A | 8/1990 | Wells |
| 4,954,129 A | 9/1990 | Giuliani et al. |
| 4,994,047 A | 2/1991 | Walker et al. |
| 5,002,526 A | 3/1991 | Herring |
| 5,009,648 A | 4/1991 | Aronoff et al. |
| 5,089,535 A | 2/1992 | Malwitz et al. |
| 5,098,535 A | 3/1992 | Nakakoshi et al. |
| 5,102,401 A | 4/1992 | Lambert et al. |
| 5,195,962 A | 3/1993 | Martin et al. |
| 5,250,028 A | 10/1993 | Theeuwes et al. |
| 5,270,086 A | 12/1993 | Hamlin |
| 5,304,205 A | 4/1994 | Shinoda et al. |
| 5,439,454 A | 8/1995 | Lo et al. |
| 5,468,526 A | 11/1995 | Allen et al. |
| 5,472,417 A | 12/1995 | Martin et al. |
| 5,569,219 A | 10/1996 | Hakki et al. |
| 5,601,538 A | 2/1997 | Deem |
| 5,616,126 A | 4/1997 | Malekmehr et al. |
| 5,643,196 A | 7/1997 | Child et al. |
| 5,688,459 A | 11/1997 | Mao et al. |
| 5,776,611 A | 7/1998 | Elton et al. |
| 5,792,114 A | 8/1998 | Fiore |
| 5,800,412 A | 9/1998 | Zhang et al. |
| 5,803,925 A | 9/1998 | Yang et al. |

(Continued)

FOREIGN PATENT DOCUMENTS

| | | |
|---|---|---|
| CN | 2240371 | 11/1996 |
| CN | 101300036 A | 11/2008 |

(Continued)

OTHER PUBLICATIONS

Extended European Search Report dated Jul. 9, 2021, in EP Application No. 21166749.8.
Rachna N. Dave, Hiren M. Joshi, and Vayalam P. Benugopalan, Novel Biocatalytic Polymer-Based Antimicrobial Coatings as Potential Ureteral Biomaterial, Feb. 1, 2011, 44(2): 845-853.
Beom Soo Kim, Jeffrey S. Hrkach, Robert Langer, Biodegradable photo-crosslinked poly(ether-ester) networks for lubricious coatings, Biomaterials, vol. 21, Issue 3, Feb. 2000, pp. 259-265.
A.K. Singla, M. Chawla, Chitosan some pharmaceutical and biological aspects, an update, Journal of Pharmacy and Pharmacology, Aug. 2001, 53: 1047-1067.
FreeStyle Vie Flushable Colostomy Bag by CliniMed Ltd., retrieved from http://www.clinimed.co.uk/Stoma-Care/Products/Closed-Stoma-Bags/Freestyle-Vie-Flushable/Product-Design.aspx Jan. 1, 2014.

(Continued)

*Primary Examiner* — Adam Marcetich
(74) *Attorney, Agent, or Firm* — Cook Alex Ltd.

(57) ABSTRACT

A medical device wherein the device has an outer surface coated with an oleophilic lubricous coating or the device is formed from a mixture including a polymer and an oleophilic compound.

17 Claims, No Drawings

(56) References Cited

U.S. PATENT DOCUMENTS

| | | |
|---|---|---|
| 5,804,653 A | 9/1998 | Weng |
| 5,902,262 A | 5/1999 | Bastioli et al. |
| 5,904,703 A | 5/1999 | Gilson |
| 5,985,394 A | 11/1999 | Mao et al. |
| 6,017,334 A | 1/2000 | Rawls |
| 6,030,369 A | 2/2000 | Engelson et al. |
| 6,063,063 A | 5/2000 | Harboe et al. |
| 6,066,120 A | 5/2000 | Whiteside |
| 6,071,618 A | 6/2000 | Cook, Jr. et al. |
| 6,090,075 A | 7/2000 | House |
| 6,168,857 B1 | 1/2001 | Anderson et al. |
| 6,213,990 B1 | 4/2001 | Roempke |
| 6,217,569 B1 | 4/2001 | Fiore |
| 6,447,835 B1 | 9/2002 | Wang et al. |
| 6,468,245 B2 | 10/2002 | Alexandersen |
| 6,471,684 B2 | 10/2002 | Dulak et al. |
| 6,488,659 B1 | 12/2002 | Rosenman |
| 6,585,721 B2 | 7/2003 | Fiore |
| 6,627,586 B1 | 9/2003 | Brooks et al. |
| 6,656,146 B1 | 12/2003 | Clayman et al. |
| 6,664,333 B2 | 12/2003 | Wang et al. |
| 6,713,140 B2 | 3/2004 | McCormack et al. |
| 6,726,654 B2 | 4/2004 | Rosenman |
| 6,787,156 B1 | 9/2004 | Bar-Shalom |
| 6,942,635 B2 | 9/2005 | Rosenblatt et al. |
| 6,960,224 B2 | 11/2005 | Marino et al. |
| 6,976,973 B1 | 12/2005 | Ruddell et al. |
| 7,037,295 B2 | 5/2006 | Tiernan et al. |
| 7,128,862 B2 | 10/2006 | Wang |
| 7,156,824 B2 | 1/2007 | Rosenman |
| 7,176,251 B1 | 2/2007 | Bastioli et al. |
| 7,182,906 B2 | 2/2007 | Chen |
| 7,402,620 B2 | 7/2008 | McGhee |
| 7,553,923 B2 | 6/2009 | Williams |
| 7,601,158 B2 | 10/2009 | ouse |
| 7,641,757 B2 | 1/2010 | Kampa et al. |
| 7,662,146 B2 | 2/2010 | House |
| 7,731,740 B2 | 6/2010 | LaFont et al. |
| 7,789,873 B2 | 9/2010 | Kubalak et al. |
| 7,815,628 B2 | 10/2010 | Devens, Jr. |
| 7,820,284 B2 | 10/2010 | Terry |
| 7,824,517 B2 | 11/2010 | Kampa et al. |
| 7,833,280 B2 | 11/2010 | Stack et al. |
| 7,947,031 B2 | 5/2011 | DiMatteo et al. |
| 8,143,368 B2 | 3/2012 | Domb et al. |
| 8,168,249 B2 | 5/2012 | Utas et al. |
| 8,187,254 B2 | 5/2012 | Hissink |
| 8,388,583 B2 | 3/2013 | Stout |
| 8,388,585 B2 | 3/2013 | Tomes |
| 8,469,928 B2 | 6/2013 | Stout |
| 8,518,019 B2 | 8/2013 | Green |
| 8,569,402 B2 | 10/2013 | Henderson et al. |
| 2002/0009561 A1 | 1/2002 | Weikel et al. |
| 2002/0016574 A1 | 2/2002 | Wang et al. |
| 2002/0051730 A1* | 5/2002 | Bodnar ................ A61F 2/915 422/33 |
| 2002/0183182 A1 | 12/2002 | Balzar et al. |
| 2003/0079297 A1 | 5/2003 | Yamakita |
| 2003/0118850 A1 | 6/2003 | McCormack et al. |
| 2003/0165647 A1 | 9/2003 | Kaneko et al. |
| 2003/0187368 A1 | 10/2003 | Sata et al. |
| 2003/0228434 A1 | 12/2003 | Bailey et al. |
| 2004/0122382 A1 | 6/2004 | Johnson et al. |
| 2004/0210180 A1 | 10/2004 | Altman |
| 2004/0220550 A1 | 11/2004 | Schryver |
| 2004/0230177 A1 | 11/2004 | DiMatteo et al. |
| 2004/0232589 A1 | 11/2004 | Kawabata et al. |
| 2005/0049577 A1 | 3/2005 | Snell et al. |
| 2005/0109648 A1 | 5/2005 | Kerzman et al. |
| 2005/0131386 A1 | 6/2005 | Freeman et al. |
| 2005/0163844 A1 | 7/2005 | Ashton |
| 2005/0170071 A1 | 8/2005 | Eramo |
| 2005/0197627 A1 | 9/2005 | Huang et al. |
| 2005/0218154 A1 | 10/2005 | Selsby |
| 2005/0244467 A1 | 11/2005 | Nivaggioli et al. |
| 2005/0277862 A1 | 12/2005 | Anand |
| 2005/0283111 A1 | 12/2005 | Maurice |
| 2006/0110498 A1 | 5/2006 | Dellinger et al. |
| 2006/0142736 A1 | 6/2006 | Hissink et al. |
| 2006/0173422 A1 | 8/2006 | Reydel et al. |
| 2006/0240064 A9 | 10/2006 | Hunter et al. |
| 2006/0246310 A1 | 11/2006 | Banks et al. |
| 2007/0009696 A1* | 1/2007 | Nakamura ................ C08L 9/00 428/446 |
| 2007/0043333 A1 | 2/2007 | Kampa et al. |
| 2007/0078412 A1 | 4/2007 | McGuckin, Jr. et al. |
| 2007/0088330 A1 | 4/2007 | House |
| 2007/0110799 A1 | 5/2007 | Leferve et al. |
| 2007/0203502 A1 | 8/2007 | Makker et al. |
| 2007/0225649 A1 | 9/2007 | House |
| 2007/0276317 A1 | 11/2007 | Henderson et al. |
| 2007/0287800 A1* | 12/2007 | Acquarulo ............ A61L 31/129 525/88 |
| 2007/0299402 A1* | 12/2007 | Ishii ...................... A61L 27/303 525/477 |
| 2008/0015527 A1 | 1/2008 | House |
| 2008/0091145 A1 | 4/2008 | House |
| 2008/0097411 A1 | 4/2008 | House |
| 2008/0118544 A1 | 5/2008 | Wang |
| 2008/0147049 A1 | 6/2008 | House et al. |
| 2008/0171991 A1 | 7/2008 | Kourakis |
| 2008/0171998 A1 | 7/2008 | House |
| 2008/0172042 A1 | 7/2008 | House |
| 2008/0176778 A1 | 7/2008 | Seemeyer et al. |
| 2008/0183262 A1 | 7/2008 | Dowling |
| 2008/0254105 A1 | 10/2008 | Tapolsky et al. |
| 2008/0255510 A1 | 10/2008 | Wang |
| 2008/0268193 A1 | 10/2008 | Cherry et al. |
| 2008/0292776 A1 | 11/2008 | Dias et al. |
| 2008/0312550 A1 | 12/2008 | Nishtala |
| 2009/0018530 A1 | 1/2009 | Nielsen et al. |
| 2009/0036874 A1 | 2/2009 | Horowitz et al. |
| 2009/0054837 A1 | 2/2009 | Von Holst et al. |
| 2009/0087607 A1* | 4/2009 | Noda ...................... C08L 53/02 524/505 |
| 2009/0110713 A1* | 4/2009 | Lim .......................... A61P 7/04 524/22 |
| 2009/0171302 A1 | 7/2009 | Eramo, Jr. et al. |
| 2009/0186783 A1 | 7/2009 | Martin et al. |
| 2009/0187162 A1* | 7/2009 | Ohara ..................... C08L 75/08 604/523 |
| 2009/0250370 A1 | 10/2009 | Whitchurch |
| 2009/0264869 A1 | 10/2009 | Schmid et al. |
| 2009/0318962 A1 | 12/2009 | Spedden et al. |
| 2010/0030197 A1 | 2/2010 | House |
| 2010/0049146 A1 | 2/2010 | Nielsen et al. |
| 2010/0098746 A1 | 4/2010 | King |
| 2010/0100116 A1 | 4/2010 | Brister et al. |
| 2010/0137743 A1 | 6/2010 | Nishtala |
| 2010/0145315 A1 | 6/2010 | House |
| 2010/0179475 A1 | 7/2010 | Hoffmann et al. |
| 2010/0198195 A1 | 8/2010 | Nishtala et al. |
| 2010/0204682 A1 | 8/2010 | Tanghoj et al. |
| 2010/0209472 A1 | 8/2010 | Wang |
| 2010/0215708 A1 | 8/2010 | Zumbuehl et al. |
| 2010/0234801 A1 | 9/2010 | Ohara et al. |
| 2010/0312255 A1 | 12/2010 | Satake et al. |
| 2010/0323189 A1 | 12/2010 | Illsley et al. |
| 2011/0049146 A1 | 3/2011 | Illsley et al. |
| 2011/0058982 A1 | 3/2011 | Kaneko |
| 2011/0071507 A1 | 3/2011 | Svensson et al. |
| 2011/0114520 A1 | 5/2011 | Matthison-Hansen |
| 2011/0129514 A1* | 6/2011 | Hossainy .................. A61P 9/00 623/1.11 |
| 2011/0160662 A1 | 6/2011 | Stout |
| 2011/0177275 A1 | 7/2011 | Morris |
| 2011/0178425 A1 | 7/2011 | Nishtala |
| 2011/0212157 A1 | 9/2011 | Edelson et al. |
| 2011/0238163 A1 | 9/2011 | Andrews et al. |
| 2011/0264057 A1 | 10/2011 | Eversull et al. |
| 2011/0268938 A1 | 11/2011 | Schuhmann |
| 2012/0035530 A1 | 2/2012 | Wang |

(56) References Cited

U.S. PATENT DOCUMENTS

| | | | |
|---|---|---|---|
| 2012/0052225 A1* | 3/2012 | Kani | C08L 29/04 428/36.6 |
| 2012/0108720 A1 | 5/2012 | Kitora et al. | |
| 2012/0121919 A1 | 5/2012 | Nielsen | |
| 2012/0219742 A1 | 8/2012 | Gravesen et al. | |
| 2013/0116662 A1 | 5/2013 | Schmid et al. | |
| 2013/0131646 A1 | 5/2013 | Gilman | |
| 2013/0158169 A1* | 6/2013 | Bond | C08L 3/00 524/51 |
| 2013/0190408 A1* | 7/2013 | Scholz | D01F 6/625 524/394 |
| 2013/0218190 A1 | 8/2013 | Gaur et al. | |
| 2013/0231693 A1 | 9/2013 | Edgren et al. | |
| 2013/0253479 A1 | 9/2013 | Su | |
| 2013/0302429 A1 | 11/2013 | Loo et al. | |
| 2013/0345681 A1 | 12/2013 | Hong | |
| 2014/0005620 A1 | 1/2014 | Wang et al. | |
| 2014/0073835 A1 | 3/2014 | Shapiro et al. | |
| 2014/0105942 A1 | 4/2014 | Pistorio et al. | |
| 2014/0309173 A1 | 10/2014 | Dreher | |
| 2015/0148461 A1 | 5/2015 | Wang et al. | |
| 2015/0152270 A1 | 6/2015 | Aizenberg et al. | |
| 2015/0274972 A1* | 10/2015 | Mateu | C08J 3/18 424/59 |
| 2016/0096006 A1 | 4/2016 | Cully et al. | |

FOREIGN PATENT DOCUMENTS

| | | |
|---|---|---|
| DE | 10 2011 119160 A1 | 5/2013 |
| EP | 0010171 A1 | 4/1980 |
| EP | 0166998 B1 | 1/1986 |
| EP | 0613672 A1 | 9/1994 |
| EP | 0628586 B1 | 12/1994 |
| EP | 0692276 A2 | 1/1996 |
| EP | 1062920 A1 | 12/2000 |
| EP | 1110561 A2 | 6/2001 |
| EP | 1415671 A1 | 5/2004 |
| EP | 2026846 A1 | 2/2009 |
| EP | 2301595 A1 | 3/2011 |
| EP | 2520412 A1 | 11/2012 |
| EP | 2609956 A1 | 7/2013 |
| GB | 2083762 | 3/1982 |
| GB | 2496901 A | 5/2013 |
| JP | S-61209655 A | 9/1986 |
| JP | 01-136662 | 9/1989 |
| JP | 11151293 | 6/1999 |
| KR | 2000/065291 A | 11/2000 |
| KR | 100754057 B | 8/2007 |
| WO | WO 89/05671 A | 6/1989 |
| WO | WO 96/41653 A1 | 12/1996 |
| WO | WO 1998/058989 A1 | 12/1998 |
| WO | WO 00/30696 A1 | 6/2000 |
| WO | WO 2006/055847 A2 | 5/2006 |
| WO | WO 2006/071813 A2 | 7/2006 |
| WO | WO 2007/122269 A1 | 11/2007 |
| WO | WO 2007/140320 A2 | 12/2007 |
| WO | WO 2010/043565 A1 | 4/2010 |
| WO | WO 2011/076211 A1 | 6/2011 |
| WO | WO 2012/163413 A1 | 12/2012 |
| WO | WO 2012/166967 A1 | 12/2012 |
| WO | WO 2014/193402 A1 | 12/2014 |

OTHER PUBLICATIONS

Australian Examination Report No. 1 for Australian Patent Application No. 2014346748 entitled: Oleophilic Lubricated Catheters, dated Jun. 19, 2017, pp. 1-3.

Australian Examination Report No. 2 for Australian Patent Application No. 2014346748 entitled: Oleophilic Lubricated Catheters, dated Sep. 26, 2017 pp. 1-6.

Australian Examination Report No. 1 for Australian Patent Application No. 2018204384 entitled: Oleophilic Lubricated Catheters, dated Jan. 2, 2019, pp. 1-4.

Australian Examination Report No. 2 for Australian Patent Application No. 2018204384 entitled: Oleophilic Lubricated Catheters, dated Sep. 19, 2019, pp. 1-2.

Communication Pursuant to Article 94(3) EPC for European Application No. 14806494.2 entitled: Oleophilic Lubricated Catheters, dated Jul. 24, 2018, pp. 1-6.

Canadian Office Action for Canadian Patent Application No. 2928646 entitled: Oleophilic Lubricated Catheters, dated Jan. 11, 2018, pp. 1-4.

Canadian Office Action for Canadian Patent Application No. 2928646 entitled: Oleophilic Lubricated Catheters, dated Sep. 20, 2018, pp. 1-4.

Canadian Office Action dated May 10, 2017, for Application No. 2,928,646 entitled: Oleophilic Lubricated Catheters.

PCT Notification of Transmittal of the International Search Report, International Search Report and Written Opinion for PCT/US2014/064254 dated Jul. 13, 2015.

* cited by examiner

OLEOPHILIC LUBRICATED CATHETERS

RELATED APPLICATION

The present application is a continuation of U.S. Nonprovisional application Ser. No. 15/034,354, filed May 4, 2016, which is the U.S. National Stage of PCT International Application No. PCT/US2014/064254, filed Nov. 6, 2014, which claims the benefit and priority of U.S. Provisional Application No. 61/901,831, filed Nov. 8, 2013, and U.S. Provisional Patent Application No. 61/944,173, filed Feb. 25, 2014, all of which are hereby incorporated herein by reference.

TECHNICAL FIELD

The present disclosure relates to lubricants for medical devices and lubricated medical devices that are inserted into the body. More particularly, the present disclosure relates to oleophilic lubricants and oleophilic lubricated medical devices for insertion into a body lumen, e.g., urinary catheters and endoscopes.

BACKGROUND

Intermittent catheterization is a good option for many users who suffer from various abnormalities of the urinary system. Urinary catheter systems typically include a long, thin, flexible tube that is inserted into the urethra, past the trigone muscle and into the bladder to drain urine from the bladder. Urine flows through the catheter and is collected, e.g., in a toilet or urine collection bag.

Catheters are commonly made from polymers, such as polyvinyl chloride (PVC) and polyurethane (PU). It is common to lubricate such catheters so as to reduce friction to allow for easier and less traumatic insertion and withdrawal of the catheter. Currently, there are two main categories of lubricated catheters, namely gel lubricated catheters and hydrophilic coated catheters.

Gel lubricated catheters are made easier to insert and withdraw by application of lubricant (such as a water-based lubricant) on the outer surface of the catheter. A catheter can be supplied with lubricant which is applied on the outer surface just before or during the packaging operation. Alternatively, lubricant can be applied to the catheter surface by a user as the catheter is being inserted into the urethra. However, the handling of gel lubricated catheters by the user can be messy, leaving lubricant on the user's hands. Further, it can increase the risk of infection from microorganisms being introduced into the body through handling of the gel lubricated catheter.

In a hydrophilic coated catheter, the catheter is provided with a thin hydrophilic coating which is applied to the outer surface of the catheter during its manufacture. The coating is activated by swelling the hydrophilic material with a hydrating agent such as liquid water, water vapor, combinations thereof and the like to provide an extremely low coefficient of friction surface. The most common form of this product is one in which a sterile, individually packaged, single use catheter is provided in a dry state or condition. The user opens the package, pours water into the package, waits a predetermined period of time, for example, 30 seconds, and then removes the catheter from the package which is ready for insertion. Some hydrophilic coated catheters are provided in a package that contains enough liquid water to cause it to be immersed. Others are provided with a separate packet of water within the package wherein the packet contains a sufficient amount of water necessary to immerse the catheter within the package. In this type of package, the packet is burst open within the package just prior to use.

One disadvantage of the hydrophilic coated catheters is that the immersion liquid has a tendency to spill from the package as the user handles the catheter and tries to remove it from the package for subsequent insertion. Further, special packaging requirements increase the complexity of such catheter systems. Another disadvantage of the hydrophilic coated catheter is that the catheter has an extremely slippery surface which makes it quite difficult for the user to handle during insertion.

Furthermore, interest in flushable catheters has been increasing. Flushable catheters may be made of water soluble polymers. Gel lubricants and hydrophilic coatings may not be suitable for use with catheters made of water soluble materials due to the water soluble material's sensitivity to water.

Therefore, there is a need for improved catheters having a lubricious surface without the user having to handle gel-lubricants and without the risk of water spillage while opening the package or activating the hydrophilic surface. The present disclosure provides improved catheters according to various embodiments to provide an alternative lubricated surface.

BRIEF SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a urinary catheter includes a catheter tube having an outer surface wherein a lubricious coating including one or more oleophilic compounds is located or disposed on the outer surface of the catheter tube.

In another aspect, a sterilized lubricated urinary catheter includes a catheter tube having an outer surface and a coating including one or more oleophilic compounds located or disposed on the outer surface of the catheter tube. The coating and catheter tube are sterilized by radiation, such as gamma or e-beam radiation.

In yet another aspect, a medical device includes an outer surface having an oleophilic lubricous coating disposed thereon, wherein the oleophilic lubricous coating is radiation sterilized and has a coefficient of friction of less than 0.2 as measured in accordance with the methods disclosed herein.

In another aspect, a catheter includes a catheter tube at least partially formed from a mixture comprising an oleophilic compound in an amount of about 0.5 percent by weight (wt. %) to about 20 wt. % of the mixture and a polymer. The catheter may be radiation sterilized. The sterilized or unsterilized catheter may have a coefficient of friction less than 0.2 as measured in accordance with the methods disclosed herein.

In yet another aspect, a method of coating a catheter tube with a lubricous coating includes placing the catheter tube into a liquid bath containing an oleophilic compound to deposit the oleophilic compound on an outer surface of the catheter. The catheter tube is removed from the liquid bath and, optionally, can be heated to anneal the oleophilic compound on the outer surface of the catheter, if desired. The catheter, optionally, may be sterilized. For example, the catheter may be sterilized with gamma radiation at a dose of between about 20 kGy and about 40 kGy. Alternatively, it could be sterilized by other known methods such as steam, ethylene oxide or electron beams.

DETAILED DESCRIPTION

While the subject matter of the present disclosure is susceptible to embodiments in various forms, there will hereinafter be described presently preferred embodiments with the understanding that the present disclosure is to be considered an exemplification and is not intended to limit the disclosure to the specific embodiments illustrated. The words "a" or "an" are to be taken to include both the singular and the plural. Conversely, any reference to plural items shall, where appropriate, include the singular.

The present disclosure is directed to lubricious medical devices that include an oleophilic lubricous coating disposed on the outer surface of the medical device to enhance the lubricity of the medical device so as to ease insertion into the human body. The present disclosure is also directed to medical devices that are made from a blend or mixture of one or more polymers and one or more oleophilic compounds wherein the addition of the oleophilic compound to the mixture enhances the lubricity of the medical device to ease insertion into the human body. The medical devices may be, for example, those which are configured for insertion into a lumen of a human body, such as the urethra, fallopian tubes, nasal passages or esophagus. Such medical devices may include, but are not limited to, urinary catheters and endoscopes. While the subject matter disclosed herein may be described relative to urinary catheters, the subject matter is not limited to such and such subject matter may apply to other suitable medical devices as well.

Urinary catheters typically include a catheter tube having an insertable portion that is inserted through the urethra and into the bladder to drain urine therefrom. The catheter tube may include a proximal end portion which is usually part of the insertable portion and is inserted through the urethra and into the bladder. The proximal end portion may have drainage eyes or holes that allow urine to drain from the bladder and through the catheter tube. The catheter tube also includes a distal end portion that may have a drainage element, such as a funnel, associated therewith to drain the urine into a collection container, such as a toilet or waste collection bag.

In one embodiment of a urinary catheter of the present disclosure, the outer surface of at least the insertable portion of the catheter has a lubricous coating including one or more oleophilic compounds disposed on the outer surface of the catheter. The oleophilic compound(s) lubricate the outer surface of the catheter for easier and less traumatic insertion of the catheter into and through the urethra.

In addition to oleophilic compounds, any of the coatings disclosed herein also may include other compounds, materials or additives as well. Such additional compounds, materials or additives may be included for any suitable purpose, such as increasing lubricity or enhancing adhesion of the coating.

Such oleophilic compounds and lubricous coatings may be especially useful with catheters made from water degradable polymers, such as water soluble polymers or polymers that deteriorate in water. Catheters made from water-degradable polymers may be designed to be disposed of by flushing the catheter down the toilet after use. For example, when placed in the toilet water, the catheter begins to dissolve or degrade so as to make it easier for the catheter material to be flushed down the toilet and through the pipes of the sanitary system. Due to the catheters' sensitivity to water (i.e., water solubility), such catheters oftentimes cannot be pre-lubricated with water based gel lubricants and/or hydrophilic coatings because the catheters may prematurely breakdown when placed in contact with the gel lubricant or a wetted hydrophilic coating.

In one embodiment, a water degradable catheter tubing may be made from any suitable water soluble polymer or any polymer that substantially deteriorates in water (e.g., by hydrolysis). One such polymer is polyvinyl alcohol (PVOH). In other embodiments, the water degradable polymers from which the tube is made may include polyacrylic acids, polylactic acid, polyesters, polyglycolide, poly lactic-co-glycolic acid, polylactide, amines, polyacrylamides, poly (N-(2-Hydroxypropyl) methacrylamide), starch, modified starches or derivatives, amylopectin, pectin, xanthan, scleroglucan, dextrin, chitosans, chitins, agar, alginate, carrageenans, laminarin, saccharides, polysaccharides, sucrose, polyethylene oxide, polypropylene oxide, acrylics, polyacrylic acid blends, poly(methacrylic acid), polystyrene sulfonate, polyethylene sulfonate, lignin sulfonate, polymethacrylamides, copolymers of aminoalkyl-acrylamides and methacrylamides, melamine-formaldehyde copolymers, vinyl alcohol copolymers, cellulose ethers, polyethers, polyethylene oxide, blends of polyethylene-polypropylene glycol, carboxymethyl cellulose, guar gum, locust bean gum, hydroxyproply cellulose, vinylpyrrolidone polymers and copolymers, polyvinyl pyrrolidone-ethylene-vinyl acetate, polyvinyl pyrrolidone-carboxymethyl cellulose, carboxymethyl cellulose shellac, copolymers of vinylpyrrolidone with vinyl acetate, hydroxyethyl cellulose, gelatin, poly-caprolactone, or combinations of any of the above materials including PVOH. The water degradable materials may also be any of those that are included in certified flushable products that meet the National Sanitation Foundation standards for flushability or materials and products that meet INDA/EDANA Flushability Guidelines. While catheters made from water degradable materials may be disposed of in a toilet, it is not necessary to dispose of such catheters in a toilet and such catheters may also be disposed in normal municipal waste systems or garbage collection systems.

In other embodiments, the catheter may be made of other polymers such as polyvinyl chloride (PVC), thermoplastic polyurethane (TPU), ethylene vinyl acetate copolymers (EVA), nylon ethylene oxide copolymers (PBAX) or blends or copolymer or multi-layer combinations of these.

The oleophilic compound that is coated on the outer surface may be any suitable oleophilic compound. Additionally, the oleophilic lubricous coating may include only one oleophilic compound or a mixture of oleophilic compounds with or without other compounds or additives.

The oleophilic compound may include, for example, an oleated glycerol, such as glycerol mono, di, tri or mixed oleates, oleyl alcohol, oleic acid, and their mixtures with themselves or other molecules may also be used. The oleophilic coating applied to the outer surface of the medical device may also include a mixture of any of the above mentioned oleophilic compounds. For example, the oleophilic coating may include a mixture of one or more glycerol oleates or one or more glycerol oleates with oleyl alcohol. In one embodiment, the oleophilic lubricious coating includes a mixture having between about 95.5 weight percent (wt. %) to about 80 wt. % of glycerol oleate(s) (one or more glycerol oleates) and about 0.5 wt. % to about 20 wt. % of oleyl alcohol. For example, the lubricious coating may include 95 wt. % glycerol oleate(s) and 5 wt. % of oleyl alcohol, or 90 wt. % glycerol oleate(s) and 10 wt. % oleyl alcohol, or 80 wt. % glycerol oleate(s) and 20 wt. % oleyl alcohol. In one embodiment, the glycerol oleate(s) are oleoyl-rac-glycerol, CAS Number 111-03-5, which is a mixture of glycerol mono, di and tri-oleates. In this embodiment, the coating may include 95 wt. % oleoyl-rac-glycerol and 5 wt. % of oleyl alcohol, or 90 wt. % oleoyl-rac-glycerol and 10 wt. % oleyl alcohol, or 80 wt. % oleoyl-rac-glycerol and 20 wt. % oleyl alcohol.

The oleophilic lubricous coating may be applied to the outer surface of the catheter or other medical device by any suitable coating process. In one method of coating the catheter with the oleophilic lubricous coating, the catheter is dipped or immersed in an oleophilic compound, such as a liquid bath of the oleophilic lubricous coating having one or more oleophilic compounds. When the oleophilic compound is a solid at room temperature, such as monooleate glycerol, the compound may be heated to melt the compound into liquid form. The catheter is left in the oleophilic lubricious coating for any suitable amount of time and in one embodiment remains in the coating from about 30 seconds to about 60 minutes or more. In one embodiment, the catheter remains in the oleophilic lubricious coating for about 1 minute to about 10 minutes. After the catheter is removed from the bath, it may be optionally heated to anneal the coating and remove any excess liquid. For example, the coated catheter may be placed in an oven heated to about 30° C. degrees to about 60° C. In one embodiment, the oven is heated to between about 40° C. to about 50° C. The catheter may remain in the oven for a time period of about 1 minute to about 24 hours. In one embodiment that catheter is placed in the oven for about 10 minutes.

As described in more detail below, the oleophilic coated catheters may have a coefficient of friction (CoF) of below 0.3 and more preferably below 0.2 as measured in accordance with the procedures described in the below Examples. In one embodiment, the catheter may comprise a water degradable catheter wherein the catheter tube is made of a water degradable polymer, such as PVOH, in which the outer surface of the catheter is coated with an oleophilic coating including one or more oleophilic compounds, such as those identified above, and has a CoF of less than about 0.45, preferably less than about 0.3 and more preferably a CoF of less than about 0.2.

When the catheter is made from a water degradable polymer, a coating may be applied to the inner and/or outer surfaces of the catheter to advantageously delay substantial dissolution or hydrolysis of the water degradable polymer such that the catheter may maintain structural integrity during handling and use. The coating may create a barrier between the water/urine and the water degradable polymer wherein the coating impedes or delays the contact between the water/urine and the soluble polymer. In one embodiment, the coating may be of a type that repels water/urine.

A coating applied to the outer surface of the catheter may, for example, delay substantial dissolution of the catheter that can result from handling of the catheter. For instance, a coating on the outer surface of the catheter may delay substantial dissolution may occur when handling the catheter with wet hands, which may be wet from washing of the hands prior to catheterization or may be wet due to sweat. A coating on the inner surface of the catheter may delay substantial dissolution of the catheter as urine passes through the catheter during drainage of the bladder.

Additionally, varying the type, amount, location of application on the catheter tube and other characteristics of the coating can be employed to tailor the dissolution/hydrolysis rate of the catheter. The ability to reduce the rate of dissolution by delaying commencement of dissolution, advantageously, may allow use of soluble polymers that are mechanically acceptable for catheter applications but dissolve too fast when exposed to water/urine.

In one embodiment, the coating for delaying substantial dissolution of the catheter includes or is any of the oleophilic compounds disclosed herein. For example, an oleophilic coating may be applied to a catheter made from any of the water degradable material enclosed herein, such as PVOH. Varying the type and amount of oleophilic coating applied may be used to vary the delay of substantial distribution.

In another embodiment, the catheter may be formed from a mixture containing a polymer and an oleophilic compound. The polymer may be any one of the water degradable polymers identified above or any other polymer identified herein. The polymer may also be ethylene-co-vinyl acetate-co-maleic anhydride polymers (EVA-MA) or ethylene-co-vinyl acetate copolymers (EVA). In one embodiment, the catheter is formed from a mixture including about 80 wt. % to about 99.5 wt. % of the polymer and about 0.5 wt. % to about 20 wt. % of an oleophilic compound or a combination of oleophilic compounds. Preferably, the mixture includes about 88 wt. % to about 97 wt. % of EVA-MA, EVA or PVC and about 3 wt. % to about 12 wt. % of an oleophilic compound or combinations thereof, and more preferably about 90 wt. % to about 95 wt. % of EVA-MA, EVA or PVC and about 10 wt. % to about 5 wt. % of an oleophilic compound or combinations thereof.

Catheters of the present disclosure also may be made by co-extrusion to form a catheter having two or more layers. In one embodiment of a co-extruded catheter, the catheter includes at least one layer formed from a mixture containing a water degradable polymer and an oleophilic compound, such as any of the above described mixtures, and another layer formed from a polymer, such as any of the water degradable polymers disclosed herein or any other suitable water degradable polymer or mixtures thereof. In one example, a catheter made from co-extrusion may be a bilayer catheter that includes an outer layer formed from a polymer/oleophilic compound mixture and an inner layer made from a water degradable polymer. The outer layer, which includes the oleophilic compound, provides a lubricious outer surface for easing insertion of the catheter into and through the urethra. The inner layer, made of the water degradable polymer, provides structural strength to the catheter to aid in handling and insertion of the catheter into the urethra. During urine drainage, the inner layer may begin dissolving and then be designed to quickly dissolve when disposed of in the toilet water after use. The dissolution of the inner layer weakens the structure of the catheter and may make it easier for the catheter to be flushed down the toilet and across the u-bend/trap of the sanitary system piping.

The polymer/oleophilic mixture layer may be a mixture of one or more of PVOH, PVC, EVA or EVA-MA with any of the oleophilic compounds disclosed herein. Additionally, the polymer to oleophilic compound ratio by weight percent may be any of those disclosed above. As mentioned above, the polymer layer may be any of the water degradable polymers disclosed herein. In one example, the thickness of the outer polymer/oleophilic layer is between about 10 micron and about 200 micron and is preferably about 50 microns. The inner layer has a thickness of between about 0.1 mm and about 1 mm and is preferably about 0.6 mm. For instance, the outer layer may be a mixture of PVOH and an oleophilic compound wherein the outer layer dissolves in water after about one hour and the inner layer may be a highly soluble PVOH that rapidly dissolves in water. Such rapidly dissolving PVOH may begin to dissolve during urine drainage and substantially dissolve soon after being place in toilet water for disposal. In another catheter, the outer layer may be a mixture of one or more of PVC, EVA or EVA-MA and an oleophilic compound and the inner layer may be a saccharide, starch or cellulose. In yet another catheter, the inner layer may be other water degradable polymers, for example any of the water degradable polymers disclosed herein.

All of the catheters or medical devices disclosed herein, optionally, may be sterilized by radiation. In one embodiment, the catheter or medical devices disclosed herein may be sterilized with gamma radiation at a dose of about 20 kGy to about 40 kGy. In one example, a catheter having an oleophilic coating thereon or a catheter made from a blend of polymer(s) and an oleophilic compound(s) may be provided in a ready to use catheter assembly wherein the catheter is sealed in a liquid and gas impermeable package, such as plastic films, an aluminum or aluminum laminated package. The package including the catheter sealed therein may be sterilized with radiation, preferably gamma radiation at a dose of about 20 kGy to about 40 kGy. In one embodiment, the catheter assembly includes a radiation sterilized catheter tube having at least the insertable length thereof coated with one or more oleophilic compounds and/or a catheter tube made from a blend or multi-layer tubes of polymers and one or more oleophilic compounds, wherein the catheter has a COF of less than about 0.45, preferably less than about 0.3 and more preferably less than about 0.2 as measured in accordance with the procedures disclosed in the below Examples. The blending of one or more oleophilic compounds with the polymer may also result in a delay of substantial dissolution of the catheter.

EXAMPLES

In Examples 1-8, tubes formed from various materials were lubricated with different oleophilic compositions. The coefficients of friction (CoF) of the oleophilic lubricated tubes were then determined as an indication for their level of lubricity. An average CoF was calculated from five different samples for each type of tube as described in more detail below.

The tubes used in the below described examples were made with a single screw extruder and had an approximate outer diameter of 4 mm and an inner diameter of 3 mm. The tubes were made from one of the below listed polymers.

Plasticized polyvinyl chloride with a shore hardness of 82 A (PVC 82A) sold under the trade name MED 7536 by Raumedic, Germany.

Polyvinyl alcohol (PVOH) sold under the trade name Mowiflex LP TC 251, supplied by Kuraray Plastics Co., Japan.

Thermoplastic polyurethane with a shore hardness of 85 A (TPU 85A) sold under the trade name Elastonllan 1185A by BASF, USA.

Plasticized polyvinyl chloride with a shore hardness of 90 A (PVC 90A) sold under the trade name Colorite PVC WU9077G-0515 90A by Colorite, USA.

Ethylene-co-vinyl acetate-co-maleic anhydride (EVA-MA) sold under the trade name Orevac 18211 by Arkema, France.

Ethylene-co-vinyl acetate (EVA) sold under the trade name Evatane 25-28 supplied by Arkema, France.

The oleophilic compositions used in the Examples described below are as follows:

Monooleate glycerol sold under the trade name Atmer 1440 by Croda International, United Kingdom.

Oleoyl-rac-glycerol, which is a mixture of mono, di and tri-oleate glycerols, supplied by SigmaAldrich, USA.

Tri-oleate glycerol sold under the trade name Priolube 1435 by Croda, United Kingdom.

Oleic acid supplied by VWR International, USA.

Oleyl alcohol supplied by VWR International, USA.

CoFs of the coated and uncoated samples of tubes, as an indicator of their lubricity, were measured using a Harland Friction Tester Model FTS5500. To determine the CoF of the tubes, a mandrel was inserted into 127 mm section of the coated or uncoated tube being tested. The tube was then clamped between two pieces of silicone rubber at 100 g load wherein the silicone rubber had a Shore hardness of 60 A. The tube with the mandrel inserted therein was pulled through the two pieces of silicone rubber at a speed of 10 mm/s. The force required to pull about 80 mm of the tube through the two pieces of silicone rubber was measured and recorded using a universal tensile tester equipped with a 200 N load cell. The CoF value was calculated from the ratio of recorded to applied loads (i.e., the recorded load divided by the applied load) when steady state was reached. At least five test runs were conducted for each type of coated tube and an average CoF value was calculated for each type of tube. For the uncoated tubing, three test runs were conducted for each sample and the average CoFs for the uncoated tubes were calculated from the three test runs.

Example 1

Sections of tubes made from PVOH were coated by a dip coating process to coat the outer surface of the tubes with glycerol monooleate. The monooleate solution was kept in an oven at 40° C., the temperature which it melts and become liquid. The PVOH tubes were dipped or placed into the melted monooleate glycerol for five minutes. The tubes were removed from the monooleate glycerol and were held for 30 seconds in the oven to drain off the excess monooleate from its surface. The average CoF was determined for the coated tubes as they were removed from the oven. The average CoF of PVOH tubes in which the outer surface was uncoated was also determined for comparison purposes.

After the initial CoF measurement, further PVOH tubing were freshly coated, removed from the solution and held inside the oven for different period of times. The PVOH coated tubes remained in the oven for time periods of 10 minutes, 20 minutes and 30 minutes. The tubes were removed from the oven at the given time period and their CoFs were measured.

In a separate test, fresh tubes of PVOH were coated with glycerol monooleate and removed from the oven. They were abraded 25 times by passing the tubes through a hole which is just smaller than the outer diameter of the tubes. The hole was punched in a 1 mm thick, silicone pad with Shore hardness of 60 A. This test was designed to remove any portions of the coating that is not well adhered to the tubes. The CoFs of the abraded tubes were measured and an average CoF was calculated for each type of tube. At room temperature, the glycerol monooleate coated on the outer surface of the PVOH tubes can re-solidify. The measurements were taken before the re-solidification. The re-solidification is more likely to occur during the abrasion test as it takes time to complete the 25 cycle.

The CoF of the coated tubes were measured according to the procedure described above and summarized in Table I below. The CoF of uncoated PVOH tubes, as control, was similarly measured. The average CoF of virgin uncoated PVOH was found to be 0.909.

TABLE I

Average CoF of PVOH Tubes Coated with Glycerol Monooleate

| Tube Samples | Avg. CoF T = 0 mins | Avg. CoF T = 10 mins | Avg. CoF T = 20 mins | Avg. CoF T = 30 mins | Avg. CoF of Abraded tubes |
|---|---|---|---|---|---|
| PVOH tubes coated with glycerol monooleate | 0.203 | 0.191 | 0.199 | 0.195 | 0.199 |

Example 2

Sections of tubes made from PVC 82A, PVC 90A, TPU 85A and PVOH were dip coated in oleoyl-rac-glycerol to coat the outer surface of the tubes. After the outer surfaces were coated, the average CoF of each type of the coated tubes was determined. The average CoF of each type of uncoated tubes was also determined for comparison purposes.

Oleoyl-rac-glycerol, a mixture of glycerol mono, di and tri-oleates, was heated in an oven set at 40° C. for 30 minutes until the oleoyl-rac-glycerol was completely melted into liquid form. The melted oleoyl-rac-glycerol was then allowed to cool, but remain in a liquid state. Each of the above-mentioned sections of tubes was dipped or placed into the melted oleoyl-rac-glycerol for five minutes. After the tubes were removed from the oleoyl-rac-glycerol they were placed in an oven set at 40° C. for 10 minutes to anneal the coating and remove excess liquid.

The CoF of the coated and uncoated tubes were measured according to the procedure described above. Additionally, coated PVC 82A, PVC 90A, TPU 85A and PVOH tubes were kept in an oven set at 23° C. and 50% relative humidity (RH) for the time periods of 10 minutes, 20 minutes and 30 minutes after which, the CoF of the tubes was measured as described above.

In measuring the CoFs of the tubes at different time intervals, a new or fresh set of tubes was used at each time interval, i.e., the tubes used at T=10 minutes were not used at T=20 minutes. In a separate test, fresh sets of tubes made of PVOH, TPU 85A and PVC 82A were coated as above and were abraded 25 times by passing the tubes through a hole which was just smaller than the outer diameter of the tubes. The hole was punched in a 1 mm thick, silicone pad with Shore hardness of 60 A. This test was designed to remove any portions of the coating that is not well adhered to the tubes. The CoFs of each of the tubes were measured and an average CoF was calculated for each type of tube. The average CoFs from Example 2 are summarized in Table II.

As shown in Table II, reductions in CoF values at T=0 were observed in the coated tubes as compared to uncoated tubes. Furthermore, the PVC 82A, PVC90A and PVOH coated tubes substantially maintained their lubricity for up to 30 minutes. Finally, the samples retain most of their low CoF values after the abrasion tests indicating the oleoyl-rac-glycerol is suitably adhered to these substrates.

TABLE II

Average CoFs for Tubes Coated with Oleoyl-rac-glycerol and Uncoated Tubes

| Tube Samples | Avg. CoF T = 0 mins | Avg. CoF T = 10 mins | Avg. CoF T = 20 mins | Avg. CoF T = 30 mins | Avg. CoF of Abraded tubes |
|---|---|---|---|---|---|
| PVOH tubes coated with oleoyl-rac-glycerol | 0.175 | 0.150 | 0.146 | 0.137 | 0.212 |
| PVOH uncoated tubes | 0.909 | — | — | — | — |
| TPU 85A tubes coated with oleoyl-rac-glycerol | 0.186 | 0.236 | — | — | 0.191 |
| TPU 85A uncoated tubes | 0.937 | — | — | — | — |
| PVC 82A tubes coated with oleoyl-rac-glycerol | 0.231 | 0.204 | 0.202 | 0.205 | 0.326 |
| PVC 82A uncoated tubes | 0.925 | — | — | — | — |
| PVC 90A tubes coated with oleoyl-rac-glycerol | 0.181 | 0.193 | 0.146 | 0.137 | — |
| PVC 90A uncoated tubes | 0.927 | — | — | — | — |

Example 3

PVC 82A and PVOH tubes were coated with oleoyl-rac-glycerol in the above-described manner. Each of the coated tubes was then individually placed in an aluminium foil packaging which was heat sealed to enclose the tube within the packaging. The aluminium packages having one of a PVC 82A or PVOH coated tube enclosed therein were sterilized using gamma radiation at nominal dose of 25 kGy. When each of the packages was opened, a post-sterilization visual inspection was conducted. No major discoloration or other damage was observed. After inspection, the CoFs of PVC 82A and PVOH coated tubes were measured at time intervals T=0 minutes after opening of the package and T=10 minutes after opening of the package. During the 10 minutes, the catheters were conditioned in an oven set at 23° C. and 50% RH. Additionally, sterilized coated PVC 82A and PVOH tubes were abraded, as described above.

The results of Example 3 are summarized in Table III which shows that the sterilized coated tubes had similar or lower CoFs as compared to the unsterilized coated tubes of Example 2. These results indicate that the polymer/oleoyl glycerol combinations are suitable for gamma sterilisation and remain substantially stable after gamma sterilization.

TABLE III

Average CoFs for Sterilized Tubes Coated with Oleoyl-rac-glycerol

| Tube Samples | Avg. CoF T = 0 mins | Avg. CoF T = 10 mins | Avg. CoF of Abraded tubes |
|---|---|---|---|
| Sterilized PVOH tubes coated with oleoyl-rac-glycerol | 0.136 | 0.129 | 0.127 |
| Sterilized PVC 82A tubes coated with oleoyl-rac-glycerol | 0.223 | 0.205 | 0.225 |

Example 4

Sections of tubes made from PVC 82A and PVOH were dip coated in glycerol tri-oleate to coat the outer surface of the tubes with glycerol tri-oleate. Similar to the previously described Examples, each of the above-mentioned sections of tubes was dipped or placed into liquid glycerol tri-oleate for five minutes. After the tubes were removed from the glycerol tri-oleate they were placed in an oven set at 40° C. for 10 minutes to anneal the coating and remove excess liquid. After the outer surfaces were coated, the average CoF of each type of the coated tubes was determined.

The CoFs of the coated tubes were measured according to the above-described procedure. After the dip coating process, the CoFs of the PVC 82A and PVOH tubes were measured at time intervals of 10, 20 and 30 minutes. During the above-defined time intervals and prior to measurement, the tubes were held in an oven set at 23° C. and 50% RH. A fresh set of tubes was used to measure the CoF at each time interval. Additionally, fresh sets of tubes were abraded as described above and the average CoF of the abraded tubes was calculated. The average CoFs of Example 4 are summarized in Table IV.

TABLE IV

Average CoF of PVOH and PVC 82A Tubes Coated with Glycerol Tri-oleate

| Tube Samples | Avg. CoF T = 0 mins | Avg. CoF T = 10 mins | Avg. CoF T = 20 mins | Avg. CoF T = 30 mins | Avg. CoF of Abraded tubes |
|---|---|---|---|---|---|
| PVOH tubes coated with glycerol tri-oleate | 0.188 | 0.169 | 0.169 | 0.175 | 0.201 |
| PVC 82A tubes coated with glycerol tri-oleate | 0.236 | 0.226 | 0.242 | 0.232 | 0.163 |

Example 5

PVC 82A and PVOH tubes were coated with glycerol tri-oleate in the manner described above in Example 4. Each of the coated tubes was then individually placed in an aluminium foil packaging which was heat sealed to enclose the tube within the packaging. Each of the aluminium packages having one of a PVC 82A or PVOH coated tube therein was sterilized using gamma radiation at a nominal dose of 25 kGy. When each of the packages was opened, a post-sterilization visual inspection was conducted and no damage to the catheter or coating was observed. After inspection, the CoFs of the PVC 82A and PVOH coated tubes were measured at time intervals 0, 10, 20 and 30 minutes. The samples were kept in an oven set at 23° C. and 50% RH for the required time prior to the measurements. Fresh sets of tubes were used to measure the CoF at each time interval. Additionally, fresh sets of PVC 82A and PVOH tubes were abraded as described above and the average CoF of the abraded tubes was calculated.

The results of Example 5 are summarized in Table V which shows that the sterilized coated tubes had substantially similar CoFs as the pre-sterile coated tubes of Example 4. These results indicate that the polymer/glycerol tri-oleate combinations are suitable for gamma sterilisation and remain substantially stable after gamma sterilization.

TABLE V

Average CoF of Sterilized PVOH and PVC 82A Tubes Coated with Tri-oleate glycerol

| Tube Samples | Avg. CoF T = 0 mins | Avg. CoF T = 10 mins | Avg. CoF T = 20 mins | Avg. CoF T = 30 mins | Avg. CoF of Abraded tubes |
|---|---|---|---|---|---|
| Sterilized PVOH tubes coated with glycerol tri-oleate | 0.211 | 0.193 | 0.232 | 0.219 | 0.187 |
| Sterilized PVC 82A tubes coated with glycerol tri-oleate | 0.391 | 0.415 | 0.339 | 0.388 | 0.297 |

Example 6

PVOH tubing was coated with a mixture of oleyl-rac-glycerol and oleyl alcohol and the average CoF was determined. Samples of PVOH were soaked in Oleoyl rac glycerol and it mixtures with Oleyl alcohol for five minutes. They were then place in an oven at 40° C. for 10 minutes to anneal and remove excess liquids. The mixtures of oleyl-rac-glycerol to oleyl alcohol that were used to coat the tubes are as follows: 100% oleyl-rac-glycerol; 95 wt. % oleyl-rac-glycerol/5 wt. % oleyl alcohol; 90 wt. % oleyl-rac-glycerol/10 wt. % oleyl alcohol; and 80 wt. % oleyl-rac-glycerol/20 wt. % oleyl alcohol. The CoFs of the PVOH tubes coated with the different mixtures of oleyl-rac-glycerol and oleyl alcohol were measured in the above described manner and the average CoFs are summarized in table VI. Additionally the CoFs of the coated tubes were measured at time intervals of 10, 20 and 30 minutes after the dip coating process. The tube samples were kept in an oven set at 23° C. and 50% RH for the above time period prior to the measurements. Fresh sets of coated tubes were used to measure the CoF at each time interval. Additionally, fresh tubes were abraded in the above discussed manner and the average CoF of the abraded tubes was calculated. As shown in Table VI, low CoF values, (i.e., high lubricity), were obtained with oleyl alcohol present.

TABLE VI

Average CoFs for Tubes Coated with Mixtures of Oleyl-rac-glycerol and Oleyl Alcohol

| Oleyl rac glycerol wt. %/ Oleyl alcohol wt. % | Avg. CoF T = 0 mins | Avg. CoF T = 10 mins | Avg. CoF T = 20 mins | Avg. CoF T = 30 mins | Avg. Abraded CoF tubes |
|---|---|---|---|---|---|
| 100%/0% | 0.192 | 0.190 | 0.187 | 0.190 | 0.154 |
| 95%/5% | 0.182 | 0.185 | 0.189 | 0.185 | 0.167 |
| 90%/10% | 0.181 | 0.182 | 0.185 | 0.186 | 0.166 |
| 80%/20% | 0.172 | 0.176 | 0.181 | 0.185 | 0.157 |

Example 7

Sections of PVOH, TPU 85A, PVC 82A and PVC 90A tubes were coated with oleic acid. Tube samples were soaked in oleic acid for five minutes after which the CoFs of the tubes were measured as described above.

The CoFs were measured after the tubes were removed from the oleic acid (T=0). The CoFs of tubes were also measured after the time intervals of 10, 20 and 30 minutes. The samples were kept in an oven set at 23° C. and 50% RH for the required time prior to the measurements. Additionally, fresh tubes were abraded in the manner described above and the average CoFs of the abraded tubes were calculated. As shown in Table VII, low CoF values were obtained for the tubes coated with oleic acid.

TABLE VII

Average CoFs of Tubes Coated with Oleic Acid

| Tubes | Avg. CoF T = 0 mins | Avg. CoF T = 10 mins | Avg. CoF T = 20 mins | Avg. CoF T = 30 mins | Avg. CoF Abraded tubes |
|---|---|---|---|---|---|
| PVOH | 0.237 | 0.222 | 0.215 | 0.253 | 0.219 |
| TPU 85A | 0.213 | 0.225 | 0.254 | 0.226 | 0.208 |
| PVC 82A | 0.196 | 0.197 | 0.211 | 0.260 | 0.203 |
| PVC 90A | 0.178 | 0.171 | 0.177 | 0.183 | 0.178 |

Example 8

A mixture of 90 wt. % of EVA and 10 wt. % glycerol monooleate was melt blended in a twin screw extruder at temperatures between 100° C. to 150° C. The mixture was then used to make tubes using a single screw extruder. Similarly, tubes were made from each of the following mixtures: EVA-MA 90 wt. %/10 wt. % glycerol monooleate 1; 90 wt. % PVC 90A/10 wt. % glycerol monooleate; and 90 wt. % PVC 90A/10 wt. % oleoyl-rac-glycerol. The CoF of each of the tubes was measured in the above-described manner. Furthermore, in a separate test, fresh tubes were abraded in the manner described above and the CoFs of the abraded tubes were measured and average CoF of each type of tube was calculated.

As shown in Table VIII, there is a reduction in CoF values for tubes made from the mixture as compared to the virgin polymers.

TABLE VIII

Average CoFs of Tubes Made from Blends of Polymers and Oleophilic Compounds And Average CoFs of Tubes Made from Virgin Polymers

| Tubes Samples | Avg. CoF | Avg. CoF of Abraded tubes |
|---|---|---|
| 90 wt. % EVA/ 10 wt. % glycerol monooleate | 0.162 | 0.255 |
| Virgin/unmodified EVA | 0.934 | — |
| 90 wt. % EVA-MA/ 10 wt. % glycerol monooleate | 0.190 | 0.259 |
| Virgin/unmodified EVA-MA | 0.925 | — |
| 90 wt. % PVC 90A/ 10 wt. % glycerol monooleate | 0.187 | 0.216 |
| 90 wt. % PVC 90A/ 10 wt. % Oleoyl-rac-glycerol | 0.161 | 0.194 |

Example 9

Bi-layer tubes of PVOH were made from coextruded PVOH polymers. The tubes included an inner layer of 8095 PVOH and an outer layer of 8120 PVOH, both supplied by G Polymer. The bi-layer tubes included an outer diameter of about 4.7 mm and an inner diameter between about 0.7 mm to about 0.8 mm.

Sections of the tube where coated with oleoyl-rac-glycerol and then dissolved in water to test the rate of dissolution of the coated tubes. Uncoated sections of the tube were also dissolved in water for comparison.

To coat the tubes, oleoyl-rac-glycerol was place in an oven heated to about 50° C. for 1 hour. The heated oleoyl-rac-glycerol was removed from the oven and 10 cm sections of the bi-layer PVOH tubes where placed in the heated oleoyl-rac-glycerol for 10 minutes and then removed.

Each of the coated and uncoated section of tubes where then cut into 5 cm pieces and separately placed in water. The water with the pieces of tubes therein was stirred with a VMS-C7 VWR stirrer at a setting of two. The time periods for which it took to dissolve 95% of the pieces of tube in the stirred water, as measured by visual indication with the naked eye, and visual observations were recorded.

As shown in Table IX below, the coated sections of tubing took a longer time to dissolve than the uncoated section.

TABLE IX

Dissolution Times for Uncoated and Oleate-Coated PVOH Tubing

| Run | Tube Samples | Volume of Water | Dissolution Time (>95% of tubing had dissolved/ no longer visible to naked eye) | Observations |
|---|---|---|---|---|
| 1 | Bi-layer PVOH tube coated with oleoyl-rac-glycerol | 80 ml | 58 mins | Couple of very small pieces or gel like materials still present at 58 minutes |
| 2 | Uncoated Bi-layer PVOH tube | 80 ml | 32 mins | Substantially dissolved at 52 mins. Pieces remaining appeared to be from cut end of tubing |
| 3 | Uncoated Bi-layer PVOH tube | 80 ml | 34 mins | Substantially dissolved at 32 minutes. One small gel from end of tubing remained present until 52 minutes |
| 4 | Bi-layer PVOH tubes coated with oleoyl-rac-glycerol | 1000 ml | 45 mins | Substantially dissolved at 45 minutes. One lump of material that was about 10% of the tube took longer than 45 minutes to dissolve At 58 minutes only small bits of fluffy material remained. |
| 5 | Uncoated Bi-layer PVOH tube | 1000 ml | 28 min | Substantially dissolved at 28 minutes. Last remaining small gel disappeared at 30 mins |

From the foregoing it will be observed that numerous modifications and variations can be effectuated without departing from the true spirit and scope of the novel concepts of the present invention. It is to be understood that no limitation with respect to the specific embodiments illustrated is intended or should be inferred. The disclosure is intended to cover by the appended claims all such modifications as fall within the scope of the claims.

Aspects of the present subject matter described above may be beneficial alone or in combination with one or more other aspects. Without limiting the foregoing description, in accordance with one aspect of the subject matter herein, there is provided a urinary catheter, which includes a catheter tube having an outer surface and a lubricious coating comprising one or more oleophilic compounds disposed on the outer surface of the catheter tube.

In accordance with a second aspect which may be used or combined with the 1st aspect the catheter tube may be comprised of a water degradable polymer.

In accordance with a third aspect which may be used or combined with the 2nd aspect the water degradable polymer may be polyvinyl alcohol.

In accordance with a fourth aspect which may be used or combined with the 1st aspect the catheter tube may be comprised of one or more of polyvinyl chloride, polyurethane, ethylene-co-vinyl acetate-co-maleic anhydride and ethylene-co-vinyl acetate.

In accordance with a fifth aspect which may be used or combined with any of the preceding aspects, the oleophilic compound may be comprised of one or more of glycerol monooleate, oleoyl-rac-glycerol, glycerol tri-oleate, oleic acid and oleyl alcohol or their mixtures.

In accordance with a sixth aspect which may be used or combined with any of the preceding aspects, the catheter has a coefficient of friction of less than about 0.45, preferably less than about 0.3 and more preferably less than about 0.2.

In accordance with a seventh aspect which may be used or combined with any of the preceding aspects, the coating may be coated onto the outer surface of the catheter tube.

In accordance with an eighth aspect which may be used or combined with any of the preceding aspects, the coating may be dip coated onto the outer surface of the catheter tube.

In accordance with a ninth aspect, there is provided a sterilized lubricated urinary catheter including a catheter tube having an outer surface, a coating comprising one or more oleophilic compounds disposed on the outer surface of the catheter tube, and wherein the coating and catheter tube are sterilized.

In accordance with a tenth aspect, which may be used or combined with the 9th aspect, the catheter tube may be comprised of a water degradable polymer.

In accordance with an eleventh aspect, which may be used or combined with the 10th aspect, the water degradable polymer may be polyvinyl alcohol.

In accordance with a twelfth aspect, which may be used or combined with the 9th aspect, the catheter tube may be comprised of one or more of polyvinyl chloride, polyurethane, ethylene-co-vinyl acetate-co-maleic anhydride and ethylene-co-vinyl acetate.

In accordance with a thirteenth aspect, which may be used or combined with any of the 9th-12th aspects, the oleophilic compound may comprise one or more of glycerol monooleate, oleoyl-rac-glycerol, glycerol tri-oleate, oleic acid and oleyl alcohol or their mixtures.

In accordance with a fourteenth aspect, which may be used or combined with any of the 9th-13th aspects, the coating may be coated onto the outer surface of the catheter tube.

In accordance with a fifteenth aspect, which may be used or combined with any of the 9th-14th aspects, the coating and catheter may be sterilized by e-beam, gamma, steam, microwave or ethylene oxide.

In accordance with a sixteenth aspect, which may be used or combined with any of the 9th-15th aspects, the radiation may be between about 20 kGy and about 40 kGy of gamma radiation.

In accordance with a seventeenth aspect which may be used or combined with any of the preceding aspects, the coating may delay substantial dissolution of the catheter.

In accordance with an eighteenth aspect which may be used or combined with any of the preceding aspects, the coating containing one or more oleophilic compounds may be applied to an inner lumen of the catheter and the coating delays substantial dissolution of the catheter.

In accordance with an nineteenth aspect, there is provided a medical device including an outer surface, and an oleophilic lubricous coating disposed on the outer surface, wherein the oleophilic lubricous coating is radiation sterilized and has a coefficient of friction of less than about 0.45 and preferably less than about 0.3 and more preferably less than about 0.2.

In accordance with a twentieth aspect which may be used or combined with the 19th aspect, the outer surface of the medical device is comprised of a water degradable polymer.

In accordance with a twenty first aspect which may be used or combined with the 20th aspect, the water degradable polymer may be polyvinyl alcohol.

In accordance with a twenty second aspect which may be used or combined with the 19th aspect, the catheter tube may be comprised of one or more of polyvinyl chloride, polyurethane, ethylene-co-vinyl acetate-co-maleic anhydride and ethylene-co-vinyl acetate.

In accordance with a twenty third aspect which may be used or combined with the any one of the 10th-22nd aspects, the oleophilic compound may comprise one or more of glycerol monooleate, oleoyl-rac-glycerol glycerol, tri-oleate, oleic acid and oleyl alcohol.

In accordance with a twenty fourth aspect which may be used or combined with any one of the 19th-22nd aspects, the coating may be dip coated onto the outer surface of the medical device.

In accordance with a twenty fifth aspect which may be used or combined with any one of the 19th-24th aspects, the coating may be gamma or e-beam sterilized.

In accordance with a twenty sixth aspect which may be used or combined with any one of the 19th-25th aspects, the radiation may be between about 20 kGy and about 40 kGy of gamma radiation.

In accordance with a twenty seventh aspect, there is provided, a catheter including a catheter tube at least partially formed from a mixture comprising an oleophilic compound and a polymer wherein the oleophilic compound is in an amount of about 0.5 percent by weight (wt. %) to about 20 wt. % of the mixture.

In accordance with a twenty eighth aspect which may be used or combined with the 27th aspect, the polymer may be in an amount of about 95.5 wt. % and 80 wt. % of the mixture.

In accordance with a twenty ninth aspect which may be used or combined with any one of the 27th and 28th aspects, the polymer may be water degradable.

In accordance with a thirtieth aspect which may be used or combined with the 29th aspect, the water degradable polymer may be polyvinyl alcohol.

In accordance with a thirty first aspect which may be used or combined with any one of the 27th and 28th aspects, the polymer may be one or more of polyvinyl chloride, polyurethane, ethylene-co-vinyl acetate-co-maleic anhydride and ethylene-co-vinyl acetate.

In accordance with a thirty second aspect which may be used or combined with any one of the 27th-31st aspects, the oleophilic compound may be one or more of glycerol monooleate, oleoyl-rac-glycerol, glycerol tri-oleate, oleic acid and oleyl alcohol.

In accordance with a thirty third aspect which may be used or combined with any one of the 27th-32nd aspects, the oleophilic compound may be about 0.5 wt. % of the mixture and the polymer is about 95.5 wt. % of the mixture.

In accordance with a thirty fourth aspect which may be used or combined with any one of the 27th-32nd aspects, the oleophilic compound may be about 5 wt. % of the mixture and the polymer is about 95 wt. % of the mixture.

In accordance with a thirty fifth aspect which may be used or combined with any one of the 27th-32nd aspects, the oleophilic compound may be about 10 wt. % of the mixture and the polymer is about 90 wt. % of the mixture.

In accordance with a thirty sixth aspect which may be used or combined with any one of the 27th-32nd aspects, the oleophilic compound may be about 15 wt. % of the mixture and the polymer is about 85 wt. % of the mixture.

In accordance with a thirty seventh aspect which may be used or combined with any one of the 27th-32nd aspects, the oleophilic compound may be about 20 wt. % of the mixture and the polymer is about 90 wt. % of the mixture.

In accordance with a thirty eighth aspect which may be used or combined with any one of the 27th-32nd aspects, the catheter may be radiation sterilized.

In accordance with a thirty ninth aspect which may be used or combined with any one of the 27th-38th aspects, the catheter may have a coefficient of friction of less than about 0.45 and preferably less than about 0.3 and more preferably less than about 0.2.

In accordance with a fortieth aspect which may be used or combined with any one of the 27th-39th aspects, the catheter may include an inner layer and an outer layer wherein the outer layer is formed from the mixture of oleophilic compound and the polymer.

In accordance with a forty first aspect which may be used or combined with the 40th aspect, the thickness of the outer layer may be between about 10 micron and about 200 micron, and preferably about 50 microns.

In accordance with a forty second aspect which may be used or combined with any one of the 40th and 41st aspects, the inner layer may be made from a water degradable polymer.

In accordance with a forty third aspect which may be used or combined with the 42nd aspect, the water degradable polymer of the inner layer may be one or more of polyvinyl alcohol, saccharide, starch or cellulose.

In accordance with a forty forth aspect, there is provided, a method of coating a catheter tube with a lubricous coating including placing the catheter tube into a liquid bath containing an oleophilic compound to deposit the oleophilic compound on an outer surface of the catheter, removing the catheter from the liquid bath, and heating the catheter to anneal the oleophilic compound on the outer surface of the catheter.

In accordance with a forty fifth aspect which may be used or combined with the 44th aspect, the method further includes melting the oleophilic compound to form the liquid bath.

In accordance with a forty sixth aspect which may be used or combined with the 44th aspect, the catheter tube may be comprised of a water degradable polymer.

In accordance with a forty seventh aspect which may be used or combined with the 46th aspect, the water degradable polymer may be polyvinyl alcohol.

In accordance with a forty eighth aspect which may be used or combined with the 44th aspect, the catheter tube may be comprised of one or more of polyvinyl chloride, polyurethane, ethylene-co-vinyl acetate-co-maleic anhydride and ethylene-co-vinyl acetate.

In accordance with a forty ninth aspect which may be used or combined with any one of the 44th-48th aspects, the oleophilic compound may comprise one or more of monooleate glycerol, oleoyl-rac-glycerol, tri-oleate glycerol, oleic acid and oleyl alcohol.

In accordance with a fiftieth aspect which may be used or combined with any one of the 44th-49th aspects, the method further includes irradiating the catheter tube having the oleophilic compound deposited thereon.

In accordance with a fifty first aspect, there is provided, a urinary catheter including a catheter tube formed from a water degradable polymer, and a coating disposed on the catheter tube, wherein the coating delays substantial dissolution of the water degradable polymer.

In accordance with a fifty second aspect which may be used or combined with the 51st aspect, the coating may comprise one or more oleophilic compounds.

In accordance with a fifty third aspect which may be used or combined with any one of the 51st and 52nd aspects, the coating may be applied to an outer surface of the catheter tube.

In accordance with a fifty forth aspect which may be used or combined with any one of the 51st-53rd aspects, the coating may be applied to an inner surface of a lumen of the catheter tube.

In accordance with a fifty fifth aspect which may be used or combined with any one of the 51st-54th aspects, the water degradable polymer may comprise PVOH.

What is claimed is:

1. A urinary catheter, comprising:
   a catheter tube at least partially formed from a mixture comprising about 0.5 percent by weight (wt. %) to about 20 wt. % oleophilic compound and a about 80 wt. % and 95.5 wt. % polymer;
   wherein the oleophilic compound is one or more of glycerol monooleate, oleoyl-rac-glycerol, glycerol trioleate, oleic acid and oleyl alcohol;
   wherein the polymer consists of one of polyvinyl alcohol, polyvinyl chloride, polyurethane, ethylene-co-vinyl acetate-co-maleic anhydride and ethylene-co-vinyl acetate.

2. The urinary catheter of claim 1 wherein the polymer is water degradable.

3. The urinary catheter of claim 1 wherein the oleophilic compound is about 0.5 wt. % of the mixture and the polymer is about 95.5 wt. % of the mixture.

4. The urinary catheter of claim 1 wherein the oleophilic compound is about 5 wt. % of the mixture and the polymer is about 95 wt. % of the mixture.

5. The urinary catheter of claim 1 wherein the oleophilic compound is about 10 wt. % of the mixture and the polymer is about 90 wt. % of the mixture.

6. The urinary catheter of claim 1 wherein the oleophilic compound is about 15 wt. % of the mixture and the polymer is about 85 wt. % of the mixture.

7. The urinary catheter of claim 1 wherein the oleophilic compound is about 20 wt. % of the mixture and the polymer is about 80 wt. % of the mixture.

8. The urinary catheter of claim 1 wherein the catheter is radiation sterilized.

9. The urinary catheter of claim 1 wherein the catheter has a coefficient of friction of less than about 0.45.

10. The urinary catheter of claim 1 wherein the catheter includes an inner layer and an outer layer wherein the outer layer is formed from the mixture of oleophilic compound and the polymer.

11. The urinary catheter of claim 10 wherein the thickness of the outer layer is between about 10 micron and about 200 micron.

12. The urinary catheter of claim 10 wherein the inner layer is made from a water degradable polymer.

13. The urinary catheter of claim 12 wherein the water degradable polymer of the inner layer is one or more of polyvinyl alcohol, saccharide, starch or cellulose.

14. A method of coating a urinary catheter tube with a lubricous coating, comprising:
- placing the catheter tube into a liquid bath containing an oleophilic compound to deposit the oleophilic compound on an outer surface of the catheter;
- removing the catheter from the liquid bath; and
- heating the catheter to anneal the oleophilic compound on the outer surface of the catheter;
- wherein the oleophilic compound is one or more of glycerol monooleate, oleoyl-rac-glycerol, glycerol tri-oleate, oleic acid and oleyl alcohol;
- wherein the catheter tube is comprised of a polymer and the polymer is one or more of polyvinyl alcohol, polyvinyl chloride, polyurethane, ethylene-co-vinyl acetate-co-maleic anhydride and ethylene-co-vinyl acetate; and
- wherein the oleophilic compound comprises between 80 wt. % and 95.5 wt. % glycerol oleates and between 0.5 wt. % and 20 wt. % oleyl alcohol.

15. The method of claim 14 further including melting the oleophilic compound to form the liquid bath.

16. The method of claim 14 wherein the catheter tube is comprised of a water degradable polymer.

17. The method of claim 14, wherein the glycerol oleates comprises one or more of glycerol monooleate, oleoyl-rac-glycerol, glycerol tri-oleate or their mixtures.

* * * * *